United States Patent [19]
Burton et al.

[11] Patent Number: 5,948,433
[45] Date of Patent: Sep. 7, 1999

[54] TRANSDERMAL PATCH

[75] Inventors: Scott Allison Burton, Essex Junction, Vt.; Shahnaz Tata, Woodstock, Ga.

[73] Assignee: Bertek, Inc., St. Albans, Vt.

[21] Appl. No.: 08/918,526

[22] Filed: Aug. 21, 1997

[51] Int. Cl.$^6$ .................................................. A61F 13/02
[52] U.S. Cl. ............................................ 424/448; 424/449
[58] Field of Search ...................................... 424/448, 449

[56] References Cited

U.S. PATENT DOCUMENTS

| | | | |
|---|---|---|---|
| 4,201,211 | 5/1980 | Chandrasekaran et al. | 424/448 |
| 4,559,222 | 12/1985 | Enscore et al. | 424/486 |
| 4,814,168 | 3/1989 | Sablotsky et al. | 514/182 |
| 4,880,416 | 11/1989 | Horiuchi et al. | 424/448 |
| 4,889,721 | 12/1989 | Ueda et al. | 424/448 |
| 4,994,267 | 2/1991 | Sablotsky | 514/763 |
| 5,164,416 | 11/1992 | Nagai et al. | 514/763 |
| 5,300,291 | 4/1994 | Sablotsky et al. | 424/78.18 |
| 5,413,794 | 5/1995 | Suzuki et al. | 424/449 |
| 5,508,038 | 4/1996 | Wang et al. | |

FOREIGN PATENT DOCUMENTS

91/16085   10/1991   WIPO.

*Primary Examiner*—D. Gabrielle Brouillette
*Attorney, Agent, or Firm*—Lerner, David, Littenberg Krumholz & Mentlik, LLP

[57] ABSTRACT

Transdermal patches are disclosed, including a backing layer, a liner layer, and a monolithic adhesive and drug-containing layer between the backing layer and the liner layer. The drug-containing adhesive layer includes polyisobutylene, a plasticizer for the polyisobutylene in which the ratio of the plasticizer and the polyisobutylene is less than about 0.8 and at least 5% of a filler. The drug so utilized is moderately soluble in the plasticizer.

29 Claims, No Drawings

TRANSDERMAL PATCH

FIELD OF THE INVENTION

The present invention relates to the field of transdermal patches. More particularly, the present invention relates to transdermal patches for applying various drugs transdermally through the skin over various time periods. Still more particularly, the present invention relates to such transdermal patches which include adhesive compositions for maintaining the transdermal patch against the skin at appropriate adhesion levels.

BACKGROUND OF THE INVENTION

The use of transdermal patches for the delivery of various drug systems has met with increasing success in the pharmaceutical industry, particularly in view of specific problems which have arisen in connection with drugs taken by other means, and because of their implications in terms of long-term application of drugs in a particularly simple manner.

One of the specific problems which has been encountered in connection with the use of various drugs has been the ability to apply a drug in a simple or monolithic system which employs the drug in admixture with an adhesive base system for application to the skin. The ability to do this with various types of drugs can be impeded by various considerations, such as differences in viscosity, solubility, therapeutic drug delivery rate, and the like.

One type of system which has been developed includes a polyisobutylene-based adhesive system preferably including a plasticizer for the polyisobutylene and a drug which is moderately soluble in that plasticizer.

One such system, for example, is set forth in Chandrasekaran et al., U.S. Pat. No. 4,201,211, which describes a five-layer therapeutic transdermal delivery system. The device in Chandrasekaran et al. specifically discloses a skin patch for administering the drug clonidine continuously and transdermally in a controlled manner for long time periods, in this case for the purpose of effecting α-andrenergic stimulation. The transdermal patch in this case includes a backing layer, a clonidine reservoir layer, a control membrane, a skin contact adhesive, and a release liner.

The particular clonidine reservoir layer employed by Chandrasekaran et al. includes, in addition to the clonidine, an organic, apolar, non-volatile, inert liquid such as mineral oil, and a blend of polyisobutylenes. These generally include mixtures of a low molecular weight polyisobutylene of 35,000 to 50,000 viscosity average molecular weight and a high molecular weight polyisobutylene of from 1 million to 1.5 million viscosity average molecular weight. The clonidine thus is carried by the mineral oil because of its limited solubility. The broad disclosure of this patent indicates that from 35% to 65% by weight of the mixture in the clonidine reservoir comprises each of the mineral oil and polyisobutylene blend. In the example in this patent, a ratio of mineral oil to polyisobutylene of about 0.9 is utilized.

In order to control the release of the drug in this case, a rate-controlling membrane is laminated between sheets of adhesive. The adhesive compositions employed in this patent demonstrate low viscosity and poor cohesive strength, and leave an unacceptable amount of residue on the skin upon removal of the patch. Furthermore, the need to use a microporous membrane not only requires great care to ensure that no air pockets arise within the membrane, but it greatly increases the complication and cost of manufacturing same.

In accordance with Enscore et al., U.S. Pat. No. 4,559,222, another transdermal patch for the delivery of a variety of drugs including clonidine is disclosed. In this system, a six-layer skin patch is disclosed including a backing layer, a drug reservoir layer, a control membrane, a skin contact adhesive layer, a prime coat layer, and a release liner. The drug delivery matrix disclosed in Enscore et al. includes mineral oil, polyisobutylene, and a moderately mineral-oil-soluble drug, along with at least 6% colloidal silicon dioxide, which is employed to increase the viscosity of the matrix composition. The compositions disclosed in this patent include a ratio of mineral oil to polyisobutylene of at least 1.0 and are characterized by viscosities of at least 1.5 times $10^7$ poise. This patentee, in fact, discloses data which is said to indicate that at increasing MO/PIB ratios the clonidine release rate also increases. Thus, such ratios below about 1.0 are said to have undesirably low drug permeability, as is specifically shown in FIG. 5 thereof.

This patentee also discloses, however, that when adding colloidal silicon dioxide the adhesion of the skin contact adhesive to the release liner is considerably increased, and as is noted in column 4 of that patent, 5 to 10 micron thick prime coats of 53% PIB/47% mineral oil were then applied between the skin contact adhesive and the liner to counteract such effects. The addition of the prime coat results, however, in a more complicated and a more costly manufacturing process. In addition, since the adhesive layer which actually contacts the skin does not contain colloidal silicon dioxide, it has a lower cohesive strength leaving residue on the skin when the system is removed.

Ueda et al., U.S. Pat. No. 4,889,721, disclose a transdermal system which includes at least two adhesive layers in which one of the layers other than the one furthest from the skin contains a solid powder which can include, inter alia, zinc oxide. The rate of drug release is thus said to be variable based upon the quantity and type of solid powder used. Clonidine is mentioned among the large number of drugs in this patent, and is mentioned as being potentially incorporated in a layer with the solid powder. Various adhesives are mentioned other than the plasticizer combination with polyisobutylene.

Sablotsky et al., U.S. Pat. Nos. 4,994,267 and 4,814,168 disclose transdermal compositions which can include large numbers of different drug compositions including clonidine. In this case, however, specific adhesive systems are mentioned including an acrylate polymer and rubber (e.g., polyisobutylene), in which materials such as zinc oxide and magnesium oxide and the like are used as cross-linking agents for carboxylic acid groups.

Wang et al., European Patent No. 525,105, disclose polyisobutylene adhesive compositions in transdermal drug delivery devices which include an oily, non-polar liquid active agent dissolved in a mixture of high molecular weight polyisobutylene and low molecular weight polyisobutylene, and in which the composition is substantially free of plasticizers and tackifiers.

Horiuchi et al., U.S. Pat. No. 4,880,416, disclose a dermal bandage including a large variety of drugs, including clonidine, in which various metal oxides, including zinc oxide, can be added to neutralize polycarboxylic acids dissolved in a vinyl acetate polymer.

Suzuki et al., U.S. Pat. No. 5,413,794, disclose drug administering systems for drugs such as clonidine, and also mention adhesion promoters, plasticizers, antioxidants, and certain unspecified fillers compounded with rubber adhesives such as polyisobutylene. Zinc oxide is mentioned as an inorganic filler for poultices containing hydrophilic polymer bases.

Sablotsky et al., U.S. Pat. No. 5,300,291, disclose the use of pressure-sensitive adhesives of mixtures of rubber, such as polyisobutylene, and a multipolymer to which clays are added for increased adhesiveness. Zinc oxide is mentioned along with calcium carbonate, silicas, and the like.

Nagai et al., U.S. Pat. No. 5,164,416 discloses the use of limonene as a penetration enhancer. Once again, zinc oxide is mentioned as an inorganic filler for poultices containing hydrophilic polymer bases.

The search has therefore continued for improved drug delivery systems for the transdermal application of drugs of this type.

SUMMARY OF THE INVENTION

In accordance with the present invention, these and other objects have now been realized by the invention of a transdermal patch for the application of a drug to the skin of a patient comprising a backing layer, a liner layer, and a drug-containing adhesive layer disposed between the backing layer and the liner layer, the drug-containing adhesive layer including polyisobutylene, a plasticizer for polyisobutylene, in which the ratio of the plasticizer and the polyisobutylene is less than about 0.8, at least 5% by weight of a filler, and a drug component comprising a drug which is moderately soluble in the plasticizer. Preferably, the ratio of the plasticizer to the polyisobutylene is between about 0.05 and 0.8.

In accordance with one embodiment of the transdermal patch of the present invention, the drug-containing adhesive layer is in direct contact with the liner layer, whereby upon removal of the liner layer and application of the transdermal patch to the skin, the adhesive layer is in direct contact with the skin.

In accordance with another embodiment of the transdermal patch of the present invention, the filler is a metal oxide, an inorganic salt, a polymeric filler, a clay component, and/or a mixture thereof. Preferably, the metal oxide can be zinc, magnesium, calcium, or titanium oxide. In another embodiment, the inorganic salts include calcium, magnesium and sodium carbonates, calcium and magnesium sulfates, and calcium phosphate. In another embodiment, the clay components include talc, kaolin, and bentonite.

In accordance with another embodiment of the transdermal patch of the present invention, the polyisobutylene comprises a mixture of high molecular weight polyisobutylene and low molecular weight polyisobutylene. Preferably, the high molecular weight polyisobutylene has a viscosity average molecular weight of between about 450,000 and 2,100,000. Preferably, the low molecular weight polyisobutylene has an average molecular weight of between about 1,000 and 450,000. Preferably, the ratio of high molecular weight polyisobutylene: low molecular weight polyisobutylene is between about 20:80 and 70:30.

In accordance with another embodiment of the transdermal patch of the present invention, the drug component includes a drug including clonidine, scopolamine, oxybutynin, lesopitron, estradiol, levonorgestrel, fentanyl, albuterol, labetolol, atropine, haloperidol, isosorbide dinitrate, nitroglycerin, norethindrone acetate, nicotine, benztropine, secoverine, dexsecoverine, and arecoline. Preferably, the drug is clonidine.

In accordance with another embodiment of the transdermal patch of the present invention, the plasticizer comprises a hydrophobic liquid, preferably having a solubility parameter of between about 12 and 18 $(J/cm^3)^{1/2}$. Preferably, the plasticizer can include mineral oil, linseed oil, octyl palmitate, squalene, squalane, silicone oil, isobutyl myristate, isostearyl alcohol, and oleyl alcohol, and the like. In a preferred embodiment mineral oil is present in an amount of between about 10 and 40 weight percent.

In accordance with a preferred embodiment of the transdermal patch of the present invention, the transdermal patch comprises a backing layer, a liner layer, and a clonidine-containing adhesive layer disposed between the backing layer and the liner layer, the clonidine-containing adhesive layer including polyisobutylene, a plasticizer comprising mineral oil for the polyisobutylene, the ratio of the mineral oil to the polyisobutylene being between about 0.5 and 0.8, and at least 5% by weight of a filler.

In accordance with one embodiment of the transdermal patch of the present invention, the patch comprises between about 10 and 40 wt. % of the mineral oil.

DETAILED DESCRIPTION

This invention is based upon a discovery that certain adhesive based drug-containing systems and transdermal patch systems can be employed utilizing polyisobutylene and a plasticizer for the polyisobutylene in combination with a drug which is moderately soluble in that plasticizer and which patches can be relatively simple in that they can be provided in the form of a monolithic patch system. That is, by a monolithic system is meant that a system in which the skin contact adhesive system and the drug itself are combined and applied to a backing layer, covered by a liner layer, and is essentially ready for use. Furthermore, the present discovery not only provides surprisingly good delivery rates of the drug for extended periods of time, but does so without the need to use a rate control membrane for application of the drug, while at the same time providing cohesively strong matrices leaving little residue on the skin upon removal of the patch itself. All of this is provided in such a system in which at least 5% by weight of filler materials are included in these drug adhesive matrices.

In particular, as compared to the prior art, it has been found also that when the filler materials of this invention are included as components in the plasticizer/polyisobutylene adhesive matrix, the degree of adhesion of that matrix to the release liner or liner layer is sufficiently low so that a separate prime coat such as that of Enscore et al., U.S. Pat. No. 4,559,222 is no longer required in order to effect ready release of the patch from the liner layer itself. Thus, by utilizing the transdermal systems of the present invention, transdermal patches for the controlled release of these drugs can be readily devised in a monolithic delivery matrix which can be used for controlled transdermal drug delivery for up to seven-day periods, again, without the use of any rate-controlling membrane therefor. The applicants have discovered that when plasticizer and polyisobutylene adhesive are utilized in which the ratio of the plasticizer to the polyisobutylene is less than about 0.8, these results are achieved, but that when such ratios greater than about 1.0 are employed, even with the filler components of the present invention, the cohesive strength of the matrix is entirely insufficient, and thus, upon removal of the patch from the skin, a residue is left thereon.

The monolithic adhesive drug-containing layer of the present invention initially includes an adhesive system of polyisobutylene and a plasticizer. The polyisobutylene itself preferably comprises a blend of a high molecular weight polyisobutylene (about 450,000 to 2,100,000 viscosity average molecular weight) and a low molecular weight polyisobutylene (about 1,000 to 450,000 viscosity average molecular weight). An example of a preferred high molecular weight polyisobutylene composition is a polyisobutylene composition sold under the designation Vistanex® L-100 having an average molecular weight of about 1,250,000 (i.e., 1.25±0.19×10⁶). An example of a preferred low molecular weight polyisobutylene composition is a polyisobutylene composition sold under the designation Vistnex® LM-MS-LC having an average molecular weight of about 45,000). In manufacturing these compositions, it is preferable to use a solvent for the polyisobutylene which is a non-solvent for the drug, such as low molecular weight hydrocarbon solvents, e.g., heptane, hexane, cyclohexane and the like with heptane being particularly preferred. Preferably, the mixture of polyisobutylene compositions includes from about 65 to 90% by weight of the solvent, more preferably from about 70 to about 85% by weight of the solvent.

In the polyisobutylene compositions of the present invention it is preferred that the high molecular weight: low molecular weight polyisobutylene in these compositions are used in a ratio of from about 20:80 to about 70:30, preferably between about 40:60 to about 50:50.

The plasticizer which is utilized in conjunction with polyisobutylene to form the adhesive layer of the present invention is a generally, inert, organic, apolar, nonvolatile hydrophobic liquid. In particular, the plasticizer is such a hydrophobic liquid in which the drug component of the present invention is moderately soluble; i.e., which has a solubility parameter of from about 12 to 18 $(J/cm^3)^{1/2}$, including various long-chain aliphatic esters and alcohols, including such materials as mineral oil, linseed oil, octyl palmitate, squalene, squalane, silicone oil, isobutyl stearate, olive oil, isopropyl myristate, isostearyl alcohol, oleyl alcohol, and the like. Preferably, the plasticizer is mineral oil of about 10 to about 14 cts at 40° C. This plasticizer acts as a carrier for the drug component which is moderately soluble therein. It is therefore necessary that the plasticizer be one in which the drug has limited solubility (for example, the solubility therein is approximately 0.1 to 10 mg/mL).

In the mixtures of plasticizer and polyisobutylene, the plasticizer generally will constitute between about 5 and 50% by weight of the mixture and the polyisobutylene correspondingly generally will constitute between about 35 and 75% by weight of the mixture. Preferably, the plasticizer will constitute between about 20 and 40% by weight of the mixture and the polyisobutylene correspondingly preferably will constitute between about 45 and 65% by weight of the mixture.

An essential component of the transdermal patch of the present invention is inclusion of at least 5% by weight of a filler in the mixture of plasticizer and polyisobutylene. The term "filler" in connection with this application signifies a filler such that a 2 to 10% w/v aqueous dispersion of the filler exhibits a pH of more than 5. Thus, such fillers include a number of inert filler components including metal oxides, inorganic salts, synthetic polymers, clays and the like. Among the various metal oxides which can be employed are zinc oxide, magnesium oxide, titanium oxide, and calcium oxide. Among the various inorganic salts which can be employed in connection with this invention are included calcium, magnesium and sodium carbonate, calcium and magnesium sulfate, calcium phosphate, and the like. Among the various synthetic polymers which can be employed as a filler in connection with this invention are included methacrylic resin, nylon, polyethylene, and the like. Among the various clay compounds which can be employed in connection with the present invention are included talc, bentonite and kaolin. It is also understood that the term "filler" in connection with this invention does not include colloidal silicon dioxide (CAB-O-SIL, for example) as is used in Enscore et al., U.S. Pat. No. 4,559,222, which is a material whose 2 to 10% w/v aqueous dispersion exhibits a pH of below 5.

Among the various drug components which can be utilized in the present invention are, as noted above, various drugs which have moderate solubility in the plasticizer. By moderate solubility is meant a drug whose solubility in mineral oil is at least 10 $\mu$g/mL and no greater than about 10 mg/mL. Thus, examples of drugs which can be used include scopolamine, clonidine, estradiol, oxybutynin, lesopitron, levonorgestrel, fentanyl, albuterol, labetolol, atropine, haloperidol, isosorbide dinitrate, nitroglycerin, norethindrone acetate, nicotine, benztropine, secoverine, dexsecoverine, and arecoline.

It is also essential in accordance with the present invention that the ratio of the plasticizer to the polyisobutylene be less than about 0.8, and preferably between about 0.05 and 0.8. Furthermore, in the case of the preferred clonidine patch utilizing the highly preferable mineral oil plasticizer hereof, the ratio of the mineral oil to the polyisobutylene will be between about 0.5 and 0.8. In any event, if that ratio is greater than about 1, such as that disclosed in the '222 patent, then the degree of adhesion will be too great and it will be difficult to remove the liner layer from the adhesive in the overall transdermal patches hereof.

In the following examples, transdermal patch systems for dispensing the drug clonidine in matrix compositions in accordance with the present invention are compared to prior art examples which contain colloidal silicon dioxide, such as Catapres-TTS®.

EXAMPLE 1

In this example, a polyisobutylene adhesive matrix was prepared by slowly mixing 11.2% (w/w) of a high molecular weight polyisobutylene (sold under the designation Vistanex® L-100) and 13.9% (w/w) of a low molecular weight polyisobutylene (sold under the designation Vistanex® LM-MS-LC) and 74.8% (w/w) normal heptane until the solution was homogeneous. The drug matrix was then prepared by homogenizing clonidine, mineral oil (12 centistokes at 40° C.), the filler material, ethanol (4% w/w) and polyisobutylene adhesive solution to produce a uniform blend. This blend is then coated onto a release liner and dried in an oven at 55° C. for five minutes and at 85° C. for ten minutes before lamination to a polyethylene terephthalate backing to yield the following compositional formulas as set forth in Table 1 hereof.

TABLE 1

|  | Percent Clonidine | Percent Mineral Oil | Percent PIB | Mo/PIB Ratio | Filler |
|---|---|---|---|---|---|
| Example #1 | 7.5 | 28.2 | 56.3 | 0.5 | 8% ZnO |
| Example #2 | 7.5 | 28.9 | 53.6 | 0.54 | 10% Talc |
| Example #3 | 7.5 | 34 | 48.5 | 0.7 | 10% ZnO |
| Example #4 | 7.5 | 37.5 | 47 | 0.8 | 8% ZnO |
| Example #5 | 7.5 | 37.5 | 47 | 0.8 | 8% MgO |
| Example #6 | 7.5 | 37.5 | 47 | 0.8 | 8% Talc |
| Example #7 | 6.8 | 30 | 53.2 | 0.56 | 10% ZnO |
| Example #8 | 7.5 | 34 | 48.5 | 0.70 | 10% Bentonite |
| Comparative | 7.5 | 36.7 | 45.8 | 0.8 | 10% CSD |

TABLE 1-continued

| | Percent Clonidine | Percent Mineral Oil | Percent PIB | Mo/PIB Ratio | Filler |
|---|---|---|---|---|---|
| Example #1 Comparative Example #2 (Catapres-TTS ®) | 7.5 | 47 | 36.7 | 1.28 | 7.5% CSD |

EXAMPLE 2

The viscosity for each of these drug matrices was determined by overlap shear tests using polished steel as a test surface at room temperature (ASTM D3654). When times to failure in a shear test are long enough in order that the initial rate of shear is low and the slip is dominated by the steady-flow viscosity, the viscosity is then given by the following formula:

$$\eta = \frac{2tMgT}{L^2W}$$

where

π=viscosity (poise)

T=time to failure (s)

L=overlap (cm)

W=width (cm)

t=thickness of adhesive interlayer (cm)

M=load (g)

g=acceleration due to gravity (981 cm/s$^2$) (C. A. Dahlquist in Creep. *Handbook of Pressure Sensitive Adhesive Technology* (2nd Ed.). edited by D. Satas, Van Nostrand Reinhold, New York (1989)).

With respect to the experimental conditions employed for each of the examples set forth in Table 1, L was 2.54 cm, W was 2.54 cm and M was 250 g. The thickness (t) of each practiced example matrix was accurately measured. Typical values were on the order of 0.009 cm. The results obtained are set forth in Table 2 below:

TABLE 2

| | Viscosity (poise) | Release from Release Liner |
|---|---|---|
| Comparative Example #1 | >1 × 10$^8$ | difficult |
| Comparative Example #2 | 5.4 × 10$^5$ | easy* |
| Example #3 | 1.8 × 10$^6$ | easy |
| Example #4 | 8.5 × 10$^5$ | easy |
| Example #5 | 1.3 × 10$^6$ | easy |
| Example #6 | 9.1 × 10$^5$ | easy |
| Example #7 | 7.0 × 10$^6$ | easy |
| Example #8 | 2.5 × 10$^6$ | easy |

*Formulation includes prime coat layer

As can be seen also from these results, the viscosity of the drug matrix in the case where the ratio of mineral oil to polyisobutylene was between about 0.5 and about 0.8 and which also contained from 8–10% of the filler was higher than the Comparative Example #2 as seen in Table 1.

As can be seen from these results, while Comparative Example #1 exhibited good cohesive strength as evidenced by its high viscosity, it did not demonstrate an easy release from the release liner because it contained colloidal silicon dioxide as discussed above. As for Comparative Example #2, although containing colloidal silicon dioxide in the drug matrix, this product had an easy release because it contained a non-colloidal silicon dioxide containing prime coat layer for interface with the release liner. However, when a non-colloidal silicon dioxide filler component in accordance with the present invention was used, release from the release liner was easy without using such a prime coat.

EXAMPLE 3

In another study, a transdermal patch was adhered to the stratum corneum of heat-separated human cadaver epidermis and mounted between glass diffusion cells (diffusion area of 2.4 cm$^2$). The receiver chamber (7 mL) was filled with 0.005M phosphate buffered isotonic saline solution (pH of 7.4) and 0.015% sodium azide to prevent microbial growth. These permeation experiments were conducted at 32° C. for one week and a receiver chamber was sampled on a daily basis. Samples were analyzed by reverse phase HPLC. The results are shown in Table 3 hereof:

TABLE 3

| | Cumulative Flux ($\mu$g/cm$^2$) Time (days) | | | | | | |
|---|---|---|---|---|---|---|---|
| | 1 | 2 | 3 | 4 | 5 | 6 | 7 |
| Example #1 | 33.0 | 89.8 | 142.7 | 189.4 | 220.6 | 249.6 | 277.6 |
| Example #2 | 37.1 | 98.7 | 159.3 | 217.0 | 257.5 | 296.4 | 335.0 |
| Example #3 | 50.0 | 105.5 | 154.1 | 200.5 | 232.5 | 262.0 | 291.1 |
| Comparative Example #1 | 67.5 | 136.5 | 195.1 | 249.5 | 286.5 | 320.9 | 354.9 |
| Comparative Example #2 | 27.3 | 71.7 | 114.4 | 156.9 | 187.8 | 219.9 | 254.1 |

As can be seen from Table 3, the transdermal flux of clonidine from those drug matrices, which contained mineral oil, polyisobutylene, 7.5% clonidine, and from 8–10% of the filler material hereof with a ratio of mineral oil to polyisobutylene of between 0.5 and 0.8, were surprisingly similar to the flux profile of Comparative Example #2 on a per/square centimeter basis. Such delivery results and profiles were obtained even though a homogeneous single layer transdermal patch was employed without a rate controlling membrane and/or without a priming layer.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A transdermal patch for the application of a drug to the skin of a patient comprising a backing layer, a liner layer, and a drug-containing adhesive layer disposed between said backing layer and said liner layer, said drug-containing adhesive layer including polyisobutylene, a plasticizer for said polyisobutylene, the ratio of said plasticizer to said polyisobutylene being less than about 0.8, at least 5% by weight of a filler, and a drug component comprising a drug which is moderately soluble in said plasticizer, said drug-containing adhesive layer being in direct contact with said liner layer without a rate control membrane therebetween, whereby upon removal of said liner layer and application of said transdermal patch to said skin, said adhesive layer is in direct contact with said skin.

2. The transdermal patch of claim 1 wherein the ratio of said plasticizer to said polyisobutylene is between about 0.05 and 0.8.

3. The transdermal patch of claim 1 wherein said filler is selected from the group consisting of metal oxides, inorganic salts, polymeric fillers, and clay components.

4. The transdermal patch of claim 3 wherein said metal oxides are selected from the group consisting of zinc, magnesium, calcium and titanium oxide.

5. The transdermal patch of claim 4 wherein said metal oxide comprises zinc oxide.

6. The transdermal patch of claim 3 wherein said inorganic salts are selected from the group consisting of calcium, magnesium and sodium carbonates, calcium and magnesium sulphates, and calcium phosphate.

7. The transdermal patch of claim 3 wherein said clay components are selected from the group consisting of talc, kaolin, and bentonite.

8. The transdermal patch of claim 1 wherein said polyisobutylene comprises a mixture of high molecular weight polyisobutylene and low molecular weight polyisobutylene.

9. The transdermal patch of claim 8 wherein said high molecular weight polyisobutylene has a viscosity average molecular weight of between about 450,000 and 2,100,000.

10. The transdermal patch of claim 9 wherein said low molecular weight polyisobutylene has an average molecular weight of between about 1,000 and 450,000.

11. The transdermal patch of claim 8 wherein the ratio of said high molecular weight polyisobutylene and said low molecular weight polyisobutylene is between about 20:80 and 70:30.

12. The transdermal patch of claim 1 wherein said drug component is selected from the group consisting of clonidine, scopolamine oxybutynin, lesopitron, estradiol, levonorgestrel, fentanyl, albuterol, labetolol, atropine, haloperidol, isosorbide dinitrate, nitroglycerin, norethindrone acetate, nicotine, benztropine, secoverine, dexsecoverine, and arecoline.

13. The transdermal patch of claim 12 wherein said drug component comprises clonidine.

14. The transdermal patch of claim 1 wherein said plasticizer comprises a hydrophobic liquid.

15. The transdermal patch of claim 14 wherein said hydrophobic liquid has a solubility parameter of between about 12 and 18 $(J/cm^3)^{1/2}$.

16. The transdermal patch of claim 12 wherein said plasticizer is selected from the group consisting of mineral oil, linseed oil, octyl palmitate, squalene, squalane, silicone oil, isobutyl myristate, isostearyl alcohol and oleyl alcohol.

17. The transdermal patch of claim 16 wherein said plasticizer comprises mineral oil.

18. The transdermal patch of claim 17 wherein said mineral oil is present in an amount of between about 10 and 40 wt. %.

19. A transdermal patch for the application of clonidine to the skin of a patient comprising a backing layer, a liner layer, and a clonidine-containing adhesive layer disposed between said backing layer and said liner layer, said clonidine-containing adhesive layer including polyisobutylene, a plasticizer comprising mineral oil for said polyisobutylene, the ratio of said mineral oil to said polyisobutylene being between about 0.5 to 0.8, and at least 5% by weight of a filler, said clonidine-containing adhesive layer being in direct contact with said liner layer without the use of a rate-control membrane therebetween, whereby upon removal of said liner layer and application of said transdermal patch to said skin, said adhesive layer is in direct contact with said skin.

20. The transdermal patch of claim 19 wherein said filler is selected from the group consisting of metal oxides, inorganic salts, polymeric fillers, and clay components.

21. The transdermal patch of claim 20 wherein said metal oxides are selected from the group consisting of zinc, magnesium, calcium and titanium oxide.

22. The transdermal patch of claim 21 wherein said metal oxide comprises zinc oxide.

23. The transdermal patch of claim 20 wherein said inorganic salts are selected from the group consisting of calcium, magnesium and sodium carbonates, calcium and magnesium sulphates, and calcium phosphate.

24. The transdermal patch of claim 20 wherein said clay components are selected from the group consisting of talc, kaolin, and bentonite.

25. The transdermal patch of claim 19 wherein said polyisobutylene comprises a mixture of high molecular weight polyisobutylene and low molecular weight polyisobutylene.

26. The transdermal patch of claim 25 wherein said high molecular weight polyisobutylene has a viscosity average molecular weight of between about 450,000 and 2,100,000.

27. The transdermal patch of claim 26 wherein said low molecular weight polyisobutylene has an average molecular weight of between about 1,000 and 450,000.

28. The transdermal patch of claim 25 wherein the ratio of said high molecular weight polyisobutylene and said low molecular weight polyisobutylene is between about 20:80 and 70:30.

29. The transdermal patch of claim 19 wherein said mineral oil is present in an amount of between about 10 and 40 wt. %.

* * * * *